(12) United States Patent
Fuhr et al.

(10) Patent No.: US 8,671,783 B2
(45) Date of Patent: Mar. 18, 2014

(54) SAMPLE CHAMBER ADAPTER, IN PARTICULAR FOR THE CRYOCONSERVATION OF BIOLOGICAL SAMPLES

(75) Inventors: Günter R. Fuhr, Berlin (DE); Heiko Zimmermann, St. Ingbert (DE); Hagen von Briesen, Hünstetten (DE); Anja Germann, Saarbrücken (DE)

(73) Assignee: Fraunhofer-Gesellschaft zur Forderung der angewandten Forschung e.V. (DE)

( * ) Notice: Subject to any disclaimer, the term of this patent is extended or adjusted under 35 U.S.C. 154(b) by 238 days.

(21) Appl. No.: 12/997,644

(22) PCT Filed: Jun. 3, 2009

(86) PCT No.: PCT/EP2009/003973
§ 371 (c)(1),
(2), (4) Date: Mar. 17, 2011

(87) PCT Pub. No.: WO2009/149853
PCT Pub. Date: Dec. 17, 2009

(65) Prior Publication Data
US 2011/0308333 A1    Dec. 22, 2011

(30) Foreign Application Priority Data
Jun. 13, 2008  (DE) .......................... 10 2008 028 334

(51) Int. Cl.
*G01N 1/42* (2006.01)
(52) U.S. Cl.
USPC ...................................... 73/863.11

(58) Field of Classification Search
None
See application file for complete search history.

(56) References Cited

U.S. PATENT DOCUMENTS

| | | | |
|---|---|---|---|
| 2,897,992 A | 8/1959 | Nungester | |
| 5,894,733 A | 4/1999 | Brodner | |
| 6,399,026 B1 * | 6/2002 | Karrai | 422/561 |
| 2007/0202017 A1 * | 8/2007 | Himmelsbach et al. | 422/102 |
| 2009/0029341 A1 | 1/2009 | Fuhr et al. | |
| 2010/0212331 A1 * | 8/2010 | Critser et al. | 62/51.1 |

FOREIGN PATENT DOCUMENTS

| | | |
|---|---|---|
| DE | 78 21 534 U1 | 10/1978 |
| DE | 37 35 708 C2 | 8/1989 |
| EP | 1 382 394 A1 | 1/2004 |
| WO | 97/18896 A1 | 5/1997 |
| WO | 2007/085385 A1 | 8/2007 |

* cited by examiner

*Primary Examiner* — Robert R Raevis
(74) *Attorney, Agent, or Firm* — DLA Piper LLP (US)

(57) ABSTRACT

An adapter device includes a receptacle including at least one receiving element that detachably secures a sample chamber for cryoconservation of a biological sample, and a coupling device that connects the receptacle to a base section which can be secured in a cooling device, wherein the receiving element is 1) immobile in a holding state at a cryoconservation temperature and secures the sample chamber and 2) at least one of deformable and movable in a release state at a temperature above the cryoconservation temperature so that the sample chamber is detachable from the adapter device or can be inserted into the adapter device.

17 Claims, 2 Drawing Sheets

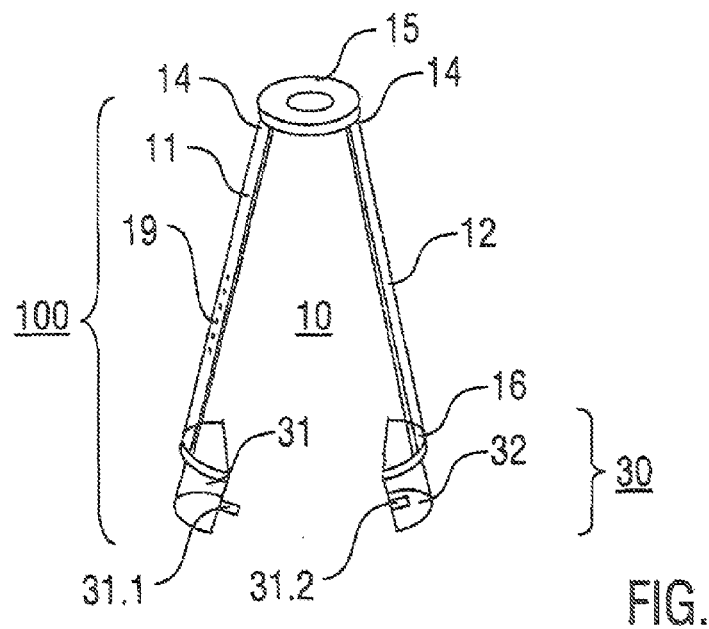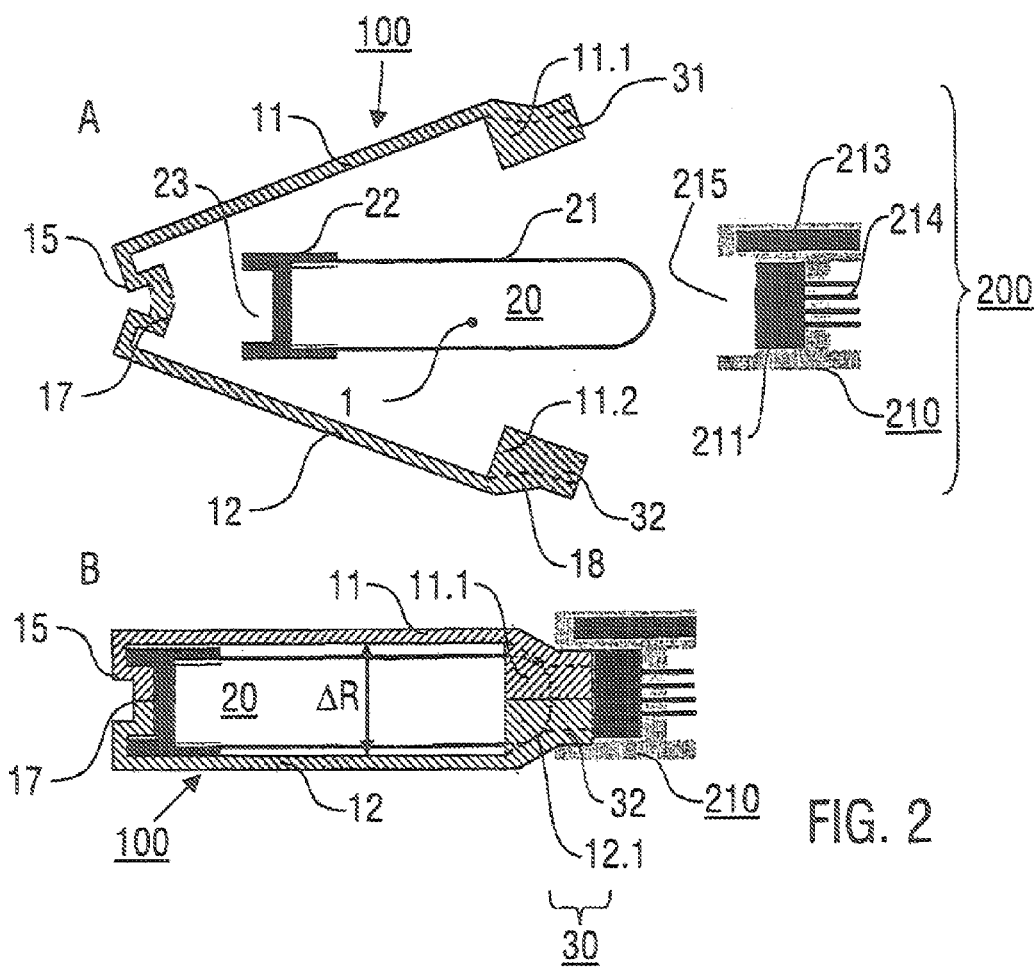

SAMPLE CHAMBER ADAPTER, IN PARTICULAR FOR THE CRYOCONSERVATION OF BIOLOGICAL SAMPLES

RELATED APPLICATIONS

This is a §371 of International Application No. PCT/EP2009/003973, with an international filing date of Jun. 3, 2009 (WO 2009/149853 A2, published Dec. 17, 2009), which is based on German Patent Application No. 10 2008 028 334.7, filed Jun. 13, 2008, the subject matter of which is incorporated by reference.

TECHNICAL FIELDS

This disclosure relates to an adapter device designed for positioning a sample chamber in a cooling device. More particularly the disclosure relates to an adapter device which is suitable to secure sample chambers of various shapes and/or sizes in the cooling device. The disclosure also relates to a sample holder device which comprises the adapter device and a sample chamber. Furthermore, the disclosure relate to a method of cryoconservation of a biological sample in which a sample chamber with the sample is arranged in the cooling device using the adapter device. Preferred applications consist in the cryoconservation of biological samples.

BACKGROUND

The freezing of biological samples for storage and/or processing (cryoconservation) is generally known. For cryoconservation, sample holders are used which are designed for receiving a sample and securing in a cooling device. A sample holder contains at least one sample chamber, the shape and size of which are selected in particular in accordance with the properties of the sample. For example, sample chambers can be in the form of capillary tubes, substrate pans or open dishes. Typically sample holders also include an electronic data storage for receiving sample data, an interface for access to the data storage and an identification device for the sample holder.

WO 97/18896 discloses a holder for sample tubes made of an elastic material and suitable for deep freezing. The holder comprises a pedestal-like base with a sample identification unit and an open-work, tubular structure in which a sample tube can be firmly held by means of a clamp connection. DE 78 21 534 U1 stands for test tubes made of folded plastic film.

For the flexible handling of a plurality of samples, a modularly constructed sample holder, described in WO 07/085,385, has proven to be advantageous. In this sample holder the sample chamber is arranged in a sleeve section. The sleeve section has ends that complement each other so that a plurality of sleeve sections can be interlocked to form one common sample holder. The sleeve section ends are also designed for connection to a base or pedestal section that can be secured in a cooling device.

A conventional sample holder is produced, for example, from plastic material in an injection molding process, whereby the sample chamber is connected in one piece with the sleeve section or, for example, can be inserted into the sleeve section as a capillary tube. The plug-type connection of the capillary tube with the sleeve section is of restricted reliability, which can be a disadvantage in practical usage conditions. There is also the risk that capillary tubes can be interchanged if the sleeve section is unintentionally separated. Furthermore, by adapting the sleeve section to a particular type of sample chamber problems can occur if samples are to be used between different cryobanks. If a sample from a first cryobank, in which a particular type of sample chamber is used, is to be transferred into another cryobank with other types of sample chambers, problems can occur with regard to securing the sample chamber and adaptation to the relevant processing of electronic sample data. With the growing use and distribution of cryobanks and the associated increased use of different types (sizes, shapes) of sample chamber, this problem has become increasingly evident in recent times. Though not intended for cryoconservation, further modular test tube or sample holders are known from DE 37 35 708 C2.

It could therefore be helpful to provide an improved adapter device for securing a sample chamber, in particular for the cryoconservation of a biological sample, with which the disadvantages and limitations in the prior art are overcome. More especially, the adapter device is to be designed to secure a sample chamber with greater reliability. In addition, the adapter device can make the integration of sample chambers of various types into existing cooling and data-processing systems possible. It could also be helpful to provide an improved sample holding device using the adapter device. It could further be helpful to provide an improved method of cryoconservation of a biological sample which overcomes the disadvantages of conventional cryoconservation methods and allows, in particular, the flexible use of sample chambers in various cooling devices.

SUMMARY

We provide an adapter device including a receptacle including at least one receiving element that detachably secures a sample chamber for cryoconservation of a biological sample, and a coupling device that connects the receptacle to a base section which can be secured in a cooling device, wherein the receiving element is 1) immobile in a holding state at a cryoconservation temperature and secures the sample chamber and 2) at least one of deformable and movable in a release state at a temperature above the cryoconservation temperature so that the sample chamber is detachable from the adapter device or can be inserted into the adapter device.

We also provide a method of cryoconservation of a biological sample, including receiving the biological sample in a sample chamber, positioning the sample chamber in the adapter device, connecting the adapter device with a base section, and securing the base section in a cooling device.

BRIEF DESCRIPTION OF THE DRAWINGS

FIG. 1 shows a schematic perspective view of a first example of an adapter device.

FIG. 2 shows a schematic illustration of a sample holding device with a further example of an adapter device.

DETAILED DESCRIPTION

Figure 3:
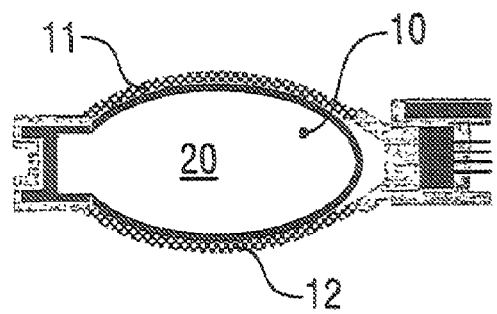
FIG. 3 shows a schematic illustration of an adapter device as shown in FIG. 1 with a clamped sample chamber.

We thus provide an adapter device having a receptacle for a sample chamber and a coupling device by which the adapter device can be positioned in a cooling device. The adapter device can be set between a holding state, in which the adapter device is at a cryoconservation temperature and in which the sample chamber is connected with the adapter device, more particularly tightly enclosed or clamped by the receptacle, and a release state in which the adapter device is at a temperature above the cryoconservation temperature, and in which the sample chamber is freely movable and can be inserted into the adapter device or detached from the adapter device. The holding state describes the simultaneous presence of a receiving state and a cryoconservation temperature. The receiving state describes a state in which the sample chamber is accommodated by the adapter device and a connection exists between them, for example, by at least partial positive lock fitting and/or mechanical tension. The cryoconservation temperature is a temperature at which a sample, more particularly an aqueous solution or suspension, is present in a frozen state in the sample chamber. The cryoconservation temperature is below −10° C., preferably below −40° C., particularly preferably below −130° C. The increased temperature of the release state is a temperature at which the at least one holder element of the adapter device can be deformed and/or moved without destruction, e.g., above 0° C. or room temperature (20° C.).

Advantageously, through setting the receptacle of the adapter device between the holding state and the release state the handling of the sample chamber can be facilitated and securing of the sample chamber to a base section or another receptacle for a further sample chamber be reliably carried out.

The receptacle comprises at least one receiving element, which in the holding state is rigid and immobile, so that the sample chamber with the at least one receiving element is fixed, and which in the release state is deformable and/or movable, so that the sample chamber can be detached from the adapter device. Advantageously, this results in the adapter device forming one unit with a secured sample chamber in the holding state, i.e., at the cryoconservation temperature. At the cryoconservation temperature the sample chamber cannot be detached from the receptacle without the latter being damaged or destroyed. In this way the reliability and security of the sample chamber holder is increased. Moreover, in the event of unwanted manipulation or incorrect handling (more particularly separation of the sample chamber from the receptacle at the cryoconservation temperature) damage to or destruction of the receptacle can be visually identified.

We also provide a sample holding device, more particularly for the cryoconservation of a biological sample, which has a sample chamber for receiving the sample and a base section for securing the sample chamber in a cooling device, whereby the sample chamber is connected to the base section by an adapter device.

The sample holding device forms a sample holder in which the base section is adapted to the coupling conditions in a particular cooling device, while there are no special requirements with regard to the type of sample chamber. As in conventional technologies, the sample holding device can fulfil additional functions with regard to the storage and processing of sample data and identification of the sample. Advantageously, the base section and/or the adapter device can fulfil the desired additional functions. Preferably, the base section and/or the adapter device contains a memory chip for the storage and/or processing of sample data, a transponder element for wireless communication with an external data-processing system, a data interface for hard-wired communication with an external data processing system and/or identification means, more particularly optical identification means. For example, the identification means, more particularly the optical identification means can be provided on the at least one receiving element of the adapter device.

If the coupling device is detachably connected to the base section, this can result in advantages for a modular structure of the sample holder device and for removal of the sample chamber in low temperature conditions. Alternatively, the coupling device can be firmly connected to the base section so that the unintentional separation of both parts can be prevented.

We further provide a method of cryoconservation of a biological sample in which the sample is arranged in a sample chamber and the sample chamber with the sample is connected to a base section by means of the adapter device and the base section is secured in a cooling device. Advantageously, the sample chamber device can be received on the adapter device at room temperature or at a cryoconservation temperature.

Preferably, the coupling device is designed so that it can only be connected to the base section when the adapter device is in the holding state. The coupling device is composed of several parts of the adapter device. Only in the holding state are these parts joined together in such a way that the connection function of the coupling device is fulfilled. In the release state the relevant parts of the adapter device are separated from each other in such a way that a connection with the base section cannot be made. The handling security of the sample chamber is increased as the latter cannot be detached from the adapter device while the coupling device is connected to the base section.

Advantageously, there are various possibilities of forming a connection between the coupling device and the base section. A screw-type connection can be provided. Advantageously, this produces a particularly secure and stable connection. A snap-lock connection can be provided, which has advantages with regard to rapid handling of the adapter device. The coupling device can be configured for a plug-type connection with the base section. The plug-type connection is advantageously of particularly simple design and allows easy adaptation of the adapter device to variously structured base sections. In contrast with the conventional insertion of capillary sample chambers into a sleeve section (see above), the plug-type connection can be designed with a tight fit and therefore increased reliability, whereby the sample chamber remains in the adapter device and is unimpaired by the plug-type connection.

Further preferably, the adapter device comprises several receiving elements, which are moveable relative to each other, such as, for example, retaining arms (clamping elements), between which the sample chamber can be gripped on at least two sides. The sample chamber can be enclosed between the retaining arms, whereby at least parts of the sample chamber, e.g., of cover and/or parts of a container are secured in a form-fitted manner or by mechanical tension. Advantageously, the retaining arms allow secure holding of the normally used sample chambers with an elongated tubular, hose or cuvette shape. For holding a sample chamber essentially extending in a predetermined longitudinal direction (axial direction) the retaining arms of the adapter device are, extending in the longitudinal direction, applied laterally (radial direction) to the sample chamber.

In addition, the at least one receiving element, more particularly the retaining arms, of the adapter device can be designed so that the sample chamber in the held state is not only enclosed in the radial, but also in the axial direction. The retaining arms may be advantageously connected at first ends via a plate (and/or at least one joint), while the coupling device is formed at the opposite, second ends. Advantageously, in this case the movement of the adapter device between the release state and the holding state is brought about in that the retaining arm are swung apart in the release state to create space for receiving the sample chamber. To move into the holding state, the retaining arms are brought together until the second ends form the coupling device. In this state, the adapter device with the sample chamber is connected to the base section to form the sample holding device.

Preferably, the adapter device, more particularly the at least one receiving element, is made of a material that precludes release of the sample chamber from the holder of the adapter device, more particularly flexible deformation in the cooled state, i.e., at a cryoconservation temperature. Preferably used for this is a synthetic material, e.g., polypropylene, HDPE, TPX (trade name) or Macrolon (trade name), which is stable at cryoconservation temperature, e.g., $-40°$ C. to $-196°$ C. The material of the receiving elements is also preferably so rigid at the cryoconservation temperature that deformation of the receiving elements is precluded and the securing of the sample chamber by partial form-fitting and/or mechanical tension cannot be undone without destroying the receiving elements. The holding state can therefore preferably not be undone at the cryoconservation temperature.

The size of the receptacle for the sample chamber can be variable. Advantageously, samples chambers of different types (size and/or shape) can therefore be secured to the adapter device in this way. Particularly preferably, the receptacle is designed so that the sample chamber can be clamped into the receptacle. We found that clamping the sample chamber to the adapter device allows reliable securing of the sample chamber both at room temperature and at a reduced temperature, more particularly cryoconservation temperature. For this purpose, the receiving elements, e.g., the retaining arms, which form the receptacle, are produced from a material that in the release state, i.e., at a release state temperature, e.g., at room temperature, is flexible, more particularly is elastically deformable. In this way at least partial form-fitting and/or mechanical tensioning can be achieved between the sample chamber and the receiving elements to bring about a holding state.

Preferably, the at least one receiving element is made of a material which at a release state temperature is flexible, preferably elastically deformable and at the cryoconservation temperature rules out deformation. In this way this example of the adapter device can be set at release temperature between the release state and the holding state, whereas this is ruled out at cryoconservation temperatures.

The receptacle of the adapter device can be designed so that a surface area of the chamber arranged in the receptacle is exposed. For example, the retaining arms can be at a lateral distance (perpendicular to the longitudinal direction of the retaining arms) through which the sample chamber is visible. Alternatively or additionally, the receptacle can be made of an at least partially transparent material through which the sample chamber is visible. This advantageously allows visual inspection of the sample chamber and/or optical measurement of the sample in the sample chamber.

The coupling device of the adapter device is generally provided for connecting the receptacle for the sample chamber with the base section or another receptacle which can be positioned in a cooling device. At least one further receptacle with at least one receiving element can be provided on the base section. Advantageously, this allows a modular structure in which a plurality of receptacles can be attached next to each other on the base section. Alternatively, several receptacles with several sample chambers can be attached to the base section stacked one on top of the other.

Further advantageously, the adapter device is suitable for use at a cryoconservation temperature down to $-200°$ C., i.e., functions as a secure holder for the sample chamber. The base section for the sample holder device is able to fulfil all the functions necessary for reliable cryoconservation. A circuit board can be applied to the base section. The base section can, if required, contain further storage or identification elements which are not provided in the case of conventional sample holders. The adapter device allows the attaching and detaching of sample chambers at all operating temperatures of a cooling device for cryoconservation, more particularly below $-130°$ C.

Advantageously, it is not absolutely necessary that for insertion into the adapter device, i.e., in the release state of the adapter device, the sample chamber is at increased temperature, e.g., room temperature. The sample chamber having the cryoconservation temperature, e.g., $<-180°$ C., can be inserted into the adapter device having an increased temperature at which the at least one receiving element is deformable and/or movable. As the adapter device has a lower thermal capacity than the sample chamber, only a minimal, non-critical temperature increase occurs on the sample chamber. The adapter device is therefore designed so that the thermal capacity (and/or mass) of the adapter is preferably less than 30%, particularly preferably less than 10%, e.g., 1% to 5% of the thermal capacity (and/or mass) of the sample chamber.

Conventional plastic substrates can be reliably taken up with the adapter device and secured in a cooling device whereby recognition of inscriptions or other means of identification, e.g., barcodes on the surface of the conventional substrates is made possible. The coupling device ensures that a held sample chamber cannot fall from the base section. Of particular advantage is the fact that a universal tool is created allowing the use of the most varied sample chambers in variously configured cooling devices of different cryobanks.

Furthermore, the adapter device is designed in a shape that matches the outer shape of the sample chamber. The outer dimensions of the adapter device with the sample chamber are practically equal to the outer dimensions of the sample chamber alone. This advantageously allows space-saving storage of samples in the cooling device.

Preferred structures are described below the reference by way of example to adapter devices in which the receptacle for the sample chamber is delimited by at least two receiving elements (retaining arms). Implementation is not restricted to the illustrated examples, but can be adapted in accordance with other configurations of the receptacle, more particularly with variable cross-sectional dimensions for adaptation to different sizes and/or shapes of the sample chamber, or with a different number of receiving elements, e.g., one receiving element or more than two receiving elements.

In the explanation, reference is made to an adapter device for an elongated sample chamber (e.g., tubes, capillaries, test tubes, with a round or angular cross-section). The sample chamber is generally a closable vessel. Typically the adapter device is designed to hold a single sample chamber. The longitudinal direction of the sample chamber and the adapter device is indicated as the axial direction, whereas the radial and azimuth directions (circumferential direction) run respectively perpendicularly or around the longitudinal direction. The adapter device can accordingly be configured for a sample chamber without a preferred longitudinal extent, e.g., for spherical or cuboid sample chambers, whereby in this case the longitudinal direction is given by a reference line running perpendicularly through a cover of the sample chamber.

The sample holder device forms a sample holder used in the cryoconservation of biological samples. The particulars of cryoconservation, such as details relating to sample preparation, the freezing process and monitoring of the samples can be implemented as known from conventional methods of cryoconservation.

Preferred examples of the adapter device 100 and the sample holding device 200 are illustrated in FIGS. 1 to 4. According to FIG. 1, the adapter device 100 has as receiving elements two retaining arms 11, 12, which facing each other at their first ends 14 are pivotably connected with a plate 15, and with a coupling device 30 being provided at their second ends 16. The retaining arms 11, 12 are in the form of straight strips with a flat or azimuthally curved surface. In the axial direction a length is provided which is selected in dependence on the length of the sample chamber, preferably in a range from 100 μm to 10 cm, more particularly from 2 cm to 5 cm. The width of the retaining arms 11, 12 is selected so that secure insertion of the sample chamber is ensured and the sample chamber remains visible between the retaining arms 11, 12. An optical identification means 19, such as a barcode, is provided on one of the retaining arms 11, 12.

As a departure from the shown illustration with two retaining arms, more retaining arms, for example, three, four or further retaining arms can be provided which can be applied laterally to the sample chamber. At least two retaining arms which face each other form the coupling device at their free ends. The plate can also be replaced by a joint. In addition, a single receiving element (a single retaining arm) can be provided which at the position of the plate 15 can be bent around the sample chamber. In this case the ends of the receiving element form the coupling device. The receiving element can also comprise a ring, which radially surrounds the sample chamber.

If two retaining arms 11, 12 are provided, the retaining arms in the azimuthal direction can comprise concavely curved strips (strips curved in a dish shape). If three or more retaining arms are provided, or if sleeve sections 11.1, 11.2 are provided for holding the sample chamber (see FIG. 2), the retaining arms can comprise flat strips.

The coupling device 30 has two cylindrical sections 31, 32 which in the assembled state (as in FIG. 2B) form a cylindrical connection element. The cylindrical sections 31, 32 are provided with a projection 31.1 and recess 32.1 which complement each other and facilitate joining (e.g., interlocking) of the cylinder sections 31, 32. If a variant is provided with three or more retaining arms the coupling device 30 is composed of three or more cylindrical sections.

The adapter device 100 is produced in one piece from a synthetic material, more particularly a transparent plastic, for example TPX (trade name). It is preferably produced by means of injection molding. At room temperature, for example, the retaining arms 11, 12 are bendable and can be swung with regard to each other on the plate 15. In the release state of the adapter device 100 (shown in FIG. 1) the retaining arms 11, 12 are swung apart to allow the sample chamber (not shown) to be inserted. To transfer the adapter device 100 into the holding state, the retaining arms 11, 12 are brought together so that the cylindrical sections 31, 32 form the cylindrical connecting element. In this state the sample chamber is tightly held between the retaining arms 11, 12 of the adapter device 100 and firmly connected to the base section, as shown in further detail in FIGS. 2 and 3. In the holding state the adapter device 100 is at a reduced temperature at which the material of the retaining arms 11, 12 is rigid and the retaining arms 11, 12 cannot be pivoted.

FIG. 2A shows the preferred example of the sample holding device 200 with an adapter device 100 in the release state. As shown in FIG. 1, the adapter device 100 comprises two retaining arms 11, 12, which on the one hand are connected by means of the plate 15 and on the other hand have cylindrical sections 31, 32 forming the coupling device 30. In contrast to the example in FIG. 1, the cylindrical sections 31, 32 have sleeve sections 11.1, 11.2 for holding the sample chamber. In the holding state of the adapter device 100 the sleeve sections 11.1, 11.2 form a hollow cylinder in which one end of the sample chamber 20 is held (see FIG. 2B).

An optional feature of the adapter device 100 is provided by oblique retaining surfaces 18, shown as a broken line in FIG. 2A between the retaining arms 11, 12 and the cylindrical sections 31, 32. The oblique retaining surfaces 18 are advantageously adapted to the tapering bottom of the sample chamber 20. Securing of the sample chamber 20 in the adapter device 100 is improved by the retaining surfaces 18.

The base section 210 comprises a plastic body into which a memory chip 211 with a data interface 214 and a transponder element 213, e.g., a RFID chip, are embedded. The basic body of the base section 210 has a receptacle 215 for forming a plug, screw or snap-lock connection with the coupling device 30 of the adapter device 100. According to modifications, the memory chip with the data interface and/or the transponder element can be provided on the adapter device 100, e.g., connected by injection molding with one of the retaining arms 11, 12 or the plate 15.

The sample chamber 20 comprises, for example, a conventional plastic tube 21 for holding the sample 1 with a cover 22. For example, a screw-type cover with a seal is provided. The sample chamber 20 is intended for holding a sample volume in the range from 25 μl to 1 l. The cover 22 can have a recess 23 into which the plate 15 engages with a projection 17 in the holding state. In this way the securing of the sample chamber 20 in the adapter device is advantageously improved. The provision of the projection 17 matching the recess 23 or any other adaptation of the adapter device to the shape of the sample chamber 20 represents an optional, but not necessarily provided feature.

FIG. 2B shows the holding state of the sample holding device 200. The retaining arms 11, 12 and the sleeve sections 11.1, 11.2 surround the sample chamber 20 in the longitudinal direction. The cylindrical sections 31, 32 form the functioning coupling device 30, for example, a connection element with an external thread. The coupling device 30 is firmly connected to the base section 210.

According to FIG. 2B the receptacle 10 is designed in such a way that the distance $\Delta R$ between the retaining arms 11, 12 without the inserted sample chamber 20 is equal to the diameter of the sample chamber 20. In this case the retaining arms 11, 12 enclose the sample chamber 20 tightly. The distance $\Delta R$ is preferably less than 10 cm, more particularly less than 2 cm, such as 15 mm or less, for example.

Alternatively, the distance between the retaining arms 11, 12 can be less than a minimum cross-sectional diameter of a sample chamber 20 to be used. If the retaining arms 11, 12 are made of an elastically deformable, expandable material (e.g., polyethylene, HDPE, polypropylene) the sample chamber can be clamped between the retaining arms 11, 12, as shown schematically in FIG. 3. In this case, the adapter device 100 can be advantageously used for various types of sample chambers.

Figure 4:
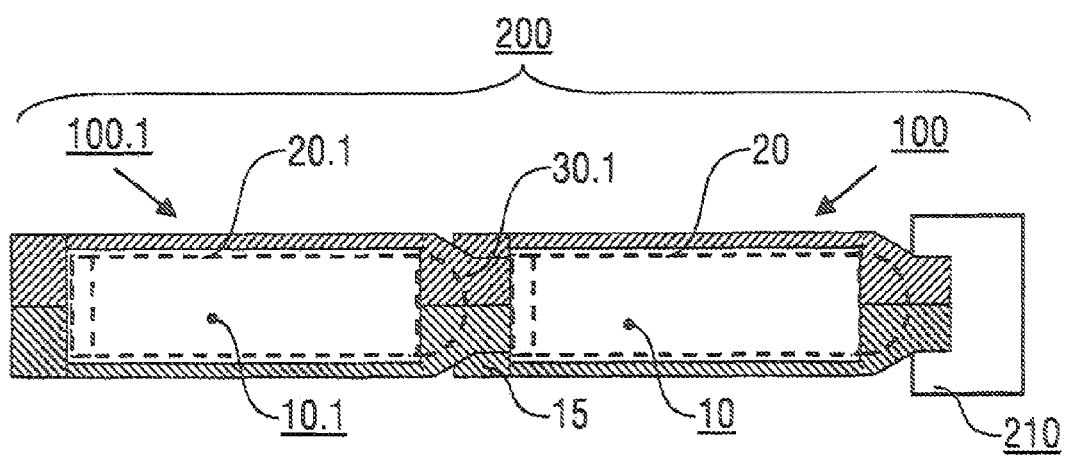
FIG. 4 shows a schematic illustration of a stack of adapter devices as shown in FIG. 2.

FIG. 4 shows a variant of the sample holding device 200 in which two adapter devices 100, 100.1 with the receptacles 10, 10.1 and each with a sample chamber 20, 20.1 are secured in a stacked manner on a common base section 210. The plate 15 of the receptacle 10 is adapted to the receptacle 10.1 for securing the coupling device 30.1. For example, the plate 15 is provided with an internal thread into which the coupling device 30.1 can be screwed. The example shown in FIG. 4 can be extended in that at least one further receptacle is secured to the receptacle 10.1.

For the cryoconservation of a biological sample, a sample chamber 20 with the sample 1 is inserted into the receptacle 10 of the adapter device 100, and the adapter device 100 is connected to the base section 210. For insertion the sample chamber 20 can be at a desired cryoconservation temperature or room temperature, whereby the adapter device 100 is in the release state and at a higher temperature. The base section 210 is secured in a cooling device (see FIG. 5).

Figure 5:
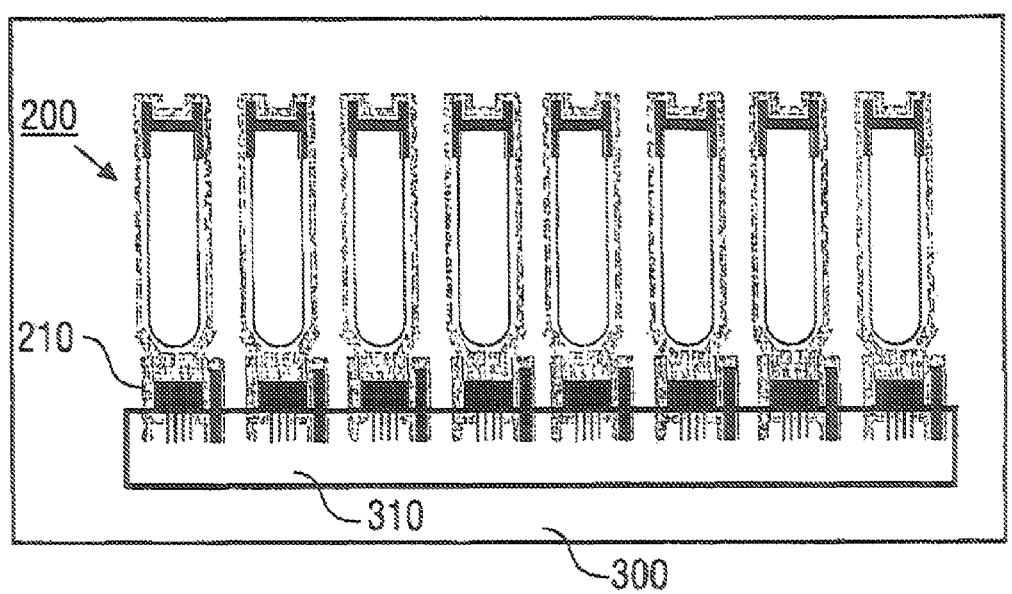
FIG. 5 shows a schematic cross-sectional view of a plurality of sample holder devices in a cooling device.

FIG. 5 shows the securing of a plurality of sample holder devices 200 on a common carrier 310 in a cooling device 300 (shown schematically). The cooling device 300 comprises, for example, a tank in which refrigeration with liquid nitrogen or with liquid nitrogen vapor is provided, as is known for the cryoconservation of biological samples. The carrier 310 comprises, for example, a circuit board onto which the base sections 210 of the sample holder devices 200 are inserted, or a shelf frame for receiving the sample holder devices.

The features disclosed in the claims, the description and in the drawing can be of relevance alone or in combination.

The invention claimed is:

1. An adapter device comprising:
 a receptacle section comprising at least one retaining arm adapted to detachably secure a sample chamber for cryoconservation of a biological sample;
 wherein
 the at least one retaining arm is adapted to be bent around the sample chamber and at least two ends of the at least one retaining arm are adapted to form a coupling section which is capable of connecting the receptacle section to a base section which can be secured in a cooling device, and
 the at least one retaining arm is 1) immobile in a holding state at a cryoconservation temperature and secures the sample chamber and 2) at least one of deformable and movable in a release state at a temperature above the cryoconservation temperature so that the sample chamber is detachable from the adapter device or can be inserted into the adapter device.

2. The adapter device according to claim 1 wherein the at least two ends of the at least one retaining arm face to each other in the holding state of the receptacle section and the coupling section forming the connection with the base section exclusively in the holding state of the receptacle.

3. The adapter device according to claim 1, wherein the coupling section forms a screw, snap-lock or plug-type connection.

4. The adapter device according to claim 1, wherein the receptacle is of variable size so that sample chambers of different sizes and/or shapes can be secured to the adapter device, or formed such that the sample chamber can be clamped in by the at least one retaining arm.

5. The adapter device according to claim 1, wherein the receptacle section of the adapter device is adapted for coupling a receptacle section of a further adapter device.

6. The adapter device according to claim 1, wherein material of the receptacle section is rigid at the cryoconservation temperature so that deformation of the at least one retaining arm is precluded and the securing of the sample chamber by partial form-fitting or mechanical tension cannot be undone without destroying the at least one retaining arm so that in the event of separation of the sample chamber from the receptacle section at the cryoconservation temperature it exhibits visible damage or destruction.

7. The adapter device according to claim 1, further comprising at least one of:
 a memory chip;
 an optical identifier;
 a transponder element; and
 a data interface.

8. A sample holder device that cryoconserves a biological sample comprising:
 at least one sample chamber that holds the biological sample; and
 a base section that secures the sample chamber in a cooling device, whereby
 the at least one sample chamber connects to the base section by least one adapter device according to claim 1.

9. The sample holder device according to claim 8, wherein the coupling section is connected to the base section.

10. The sample holder device according to claim 8, wherein the base section and/or the adapter device contains at least one of;
 a memory chip;
 an optical identifier;
 a transponder clement; and
 a data interface.

11. A method of cryoconservation of a biological sample, comprising:
 receiving the biological sample in a sample chamber;
 positioning the sample chamber in an adapter device according to claim 1;
 connecting the adapter device with a base section; and
 securing the base section in a cooling device.

12. The device according to claim 1, wherein the at least one retaining arm is made of a material which precludes flexible deformation in the holding at the cryoconservation temperature and which is flexible in the release state at the temperature above the cryoconservation temperature.

13. An adapter device comprising:
 a receptacle section adapted to detachably secure a sample chamber for cryoconservation of a biological sample and comprising at least one retaining arm and at least two free retaining arm ends;
 wherein
 the at least one retaining arm is adapted to enclose the sample chamber and the at least two free retaining arm ends are adapted to assemble together to jointly form a coupling section which is capable of connecting the receptacle section to a base section which can be secured in a cooling device, and
 the at least one retaining arm is 1) immobile in a holding state at a cryoconservation temperature and secures the sample chamber and 2) at least one of deformable and movable in a release state at a temperature above the cryoconservation temperature so that the sample chamber is detachable from the adapter device or can be inserted into the adapter device.

14. The adaptor device according to claim 13, wherein
 the receptacle section comprises multiple retaining arms between which the sample chamber can be locked.

15. The adapter device, according to claim 14, wherein the retaining arms have first ends connected to each other by a plate or at least one joint, and second ends which are adapted to form the coupling section.

16. The adapter device according to claim 15, wherein at least one of the plate and the at least one joint is rigid at the cryoconservation temperature.

17. The adapter device according to claim 13, comprising multiple retaining arms, which
- have sleeve sections for holding the sample chamber between which the sample chamber can be enclosed;
- are a lateral distance from each other so that a surface area of the held sample chamber is exposed; or
- are at least partially transparent.

\* \* \* \* \*